United States Patent
Clauson et al.

(10) Patent No.: US 10,363,029 B2
(45) Date of Patent: Jul. 30, 2019

(54) NEEDLE FOR DELIVERY OF DERMAL FILLER THREADS

(71) Applicant: Allergan Holdings France S.A.S., Courbevoie (FR)

(72) Inventors: Luke Clauson, Redwood City, CA (US); Matthew Newell, Redwood City, CA (US); Kenneth N. Horne, San Francisco, CA (US); Darin Gittings, Sunnyvale, CA (US)

(73) Assignee: Allergan Holdings France S.A.S., Courbevoie (FR)

( * ) Notice: Subject to any disclaimer, the term of this patent is extended or adjusted under 35 U.S.C. 154(b) by 18 days.

(21) Appl. No.: 15/267,060

(22) Filed: Sep. 15, 2016

(65) Prior Publication Data

US 2017/0000944 A1    Jan. 5, 2017

Related U.S. Application Data

(63) Continuation of application No. 14/126,741, filed as application No. PCT/US2012/042800 on Jun. 15, 2012, now abandoned.

(Continued)

(51) Int. Cl.
*A61B 17/06* (2006.01)
*A61M 5/158* (2006.01)
(Continued)

(52) U.S. Cl.
CPC .... *A61B 17/06004* (2013.01); *A61B 17/3468* (2013.01); *A61M 5/158* (2013.01); *A61M 5/32* (2013.01); *A61B 2017/00792* (2013.01); *A61B 2017/06028* (2013.01); *A61L 17/10* (2013.01); *A61L 17/12* (2013.01); *A61L 2430/34* (2013.01)

(58) Field of Classification Search
CPC ............. A61M 5/158; A61B 17/06004; A61B 17/06066; A61B 17/06071; A61B 17/06114; A61B 17/06128; A61B 17/12; A61B 17/34; A61B 17/3431; A61B 17/3496; A61B 2017/045; A61B 2017/0454; A61B 2017/1132; A61B 17/1152; A61B 17/1155
See application file for complete search history.

(56) References Cited

U.S. PATENT DOCUMENTS 299,305 A  *  5/1884  Weed ........................ D07B 7/18
                                                  606/225
1,678,361 A  *  7/1928  Shearon ........... A61B 17/06004
                                                  403/59

(Continued)

FOREIGN PATENT DOCUMENTS

WO       199001349 A1     2/1990
WO      2010028025 A1     3/2010
(Continued)

*Primary Examiner* — Sarah W Aleman
(74) *Attorney, Agent, or Firm* — Nathan S. Smith; Morgan, Lewis & Bockius LLP

(57) ABSTRACT

Provided herewith is a needle for delivering dermal filler thread to a wrinkle in a patient. The needle can also be used to deliver the thread to a patient for the purposes of facial contouring. The needle comprises a coupler for attaching the thread to the needle and also a trocar to ease delivery through the skin.

20 Claims, 18 Drawing Sheets

Related U.S. Application Data

(60) Provisional application No. 61/498,364, filed on Jun. 17, 2011.

(51) Int. Cl.
*A61M 5/32* (2006.01)
*A61B 17/34* (2006.01)
*A61L 17/10* (2006.01)
*A61L 17/12* (2006.01)
*A61B 17/00* (2006.01)

(56) References Cited

U.S. PATENT DOCUMENTS

| | | | | |
|---|---|---|---|---|
| 2,302,986 | A * | 11/1942 | Vollrath | A61B 17/06004 24/265 A |
| 2,581,564 | A * | 1/1952 | Villegas | A61B 17/06004 223/102 |
| 3,880,167 | A * | 4/1975 | Hardwick | A61B 17/06004 606/225 |
| 3,910,282 | A | 10/1975 | Messer et al. | |
| 5,116,358 | A * | 5/1992 | Granger | A61B 17/06004 606/224 |
| 5,478,327 | A | 12/1995 | McGregor et al. | |
| 5,752,970 | A * | 5/1998 | Yoon | A61B 17/3421 604/167.03 |
| 7,998,170 | B2 * | 8/2011 | Cunningham | A61B 17/06066 606/223 |
| 2008/0119876 | A1 | 5/2008 | Price et al. | |
| 2011/0152926 | A1 | 6/2011 | Vetrecin | |
| 2011/0263724 | A1 * | 10/2011 | Gurtner | A61L 15/28 514/777 |
| 2012/0245629 | A1 | 9/2012 | Gross et al. | |
| 2016/0007990 | A1 | 1/2016 | Solish et al. | |

FOREIGN PATENT DOCUMENTS

| | | |
|---|---|---|
| WO | 2011109129 A1 | 9/2011 |
| WO | 2011109130 A1 | 9/2011 |
| WO | 2012174464 A3 | 5/2014 |

\* cited by examiner

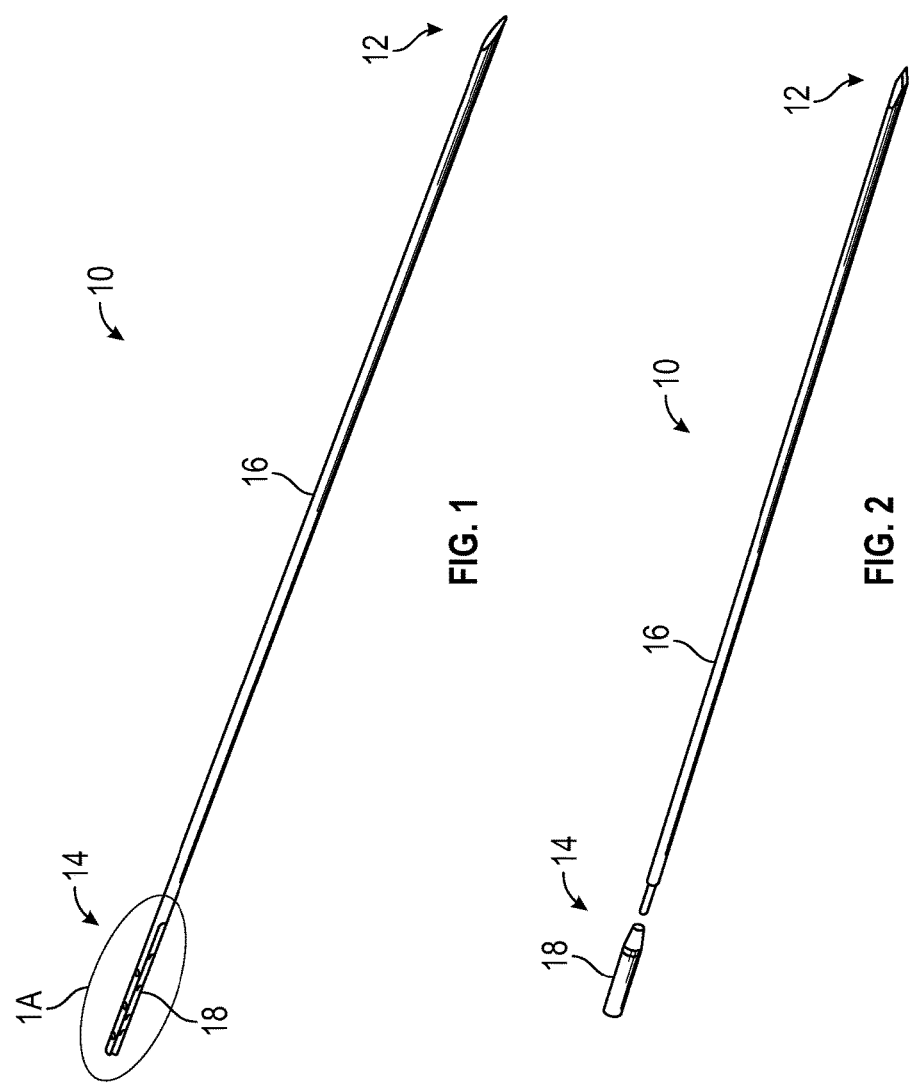

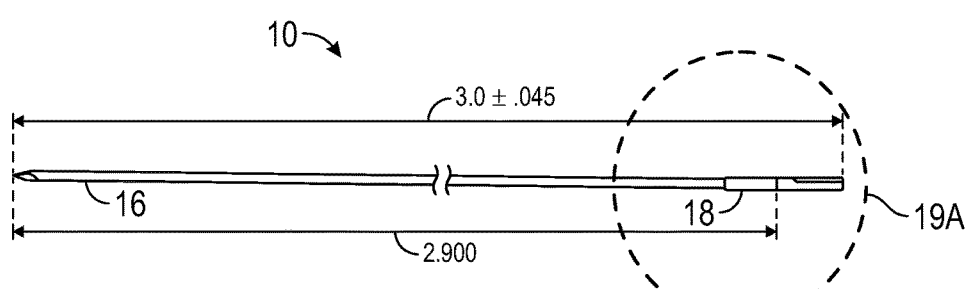
FIG. 19
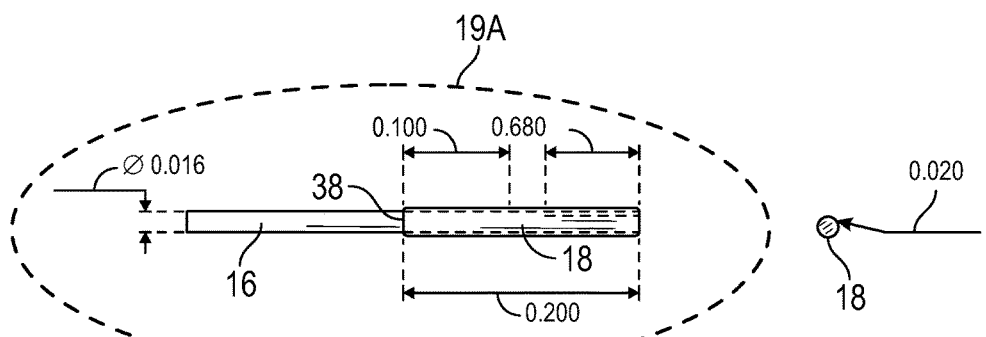
FIG. 20
FIG. 21

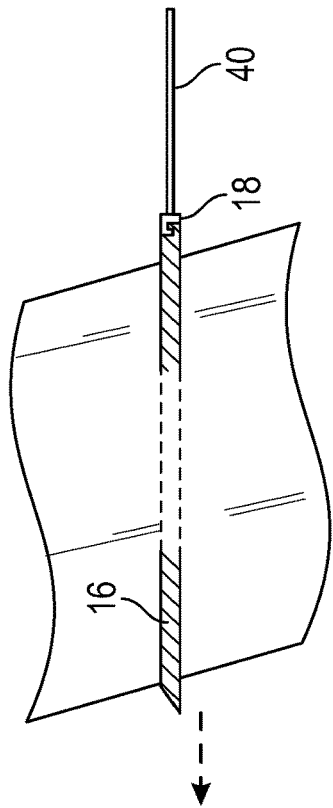
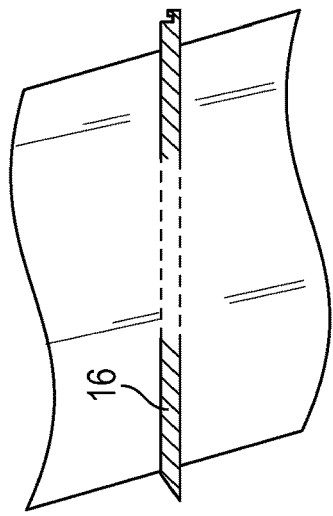

NEEDLE FOR DELIVERY OF DERMAL FILLER THREADS

CROSS-REFERENCE TO RELATED APPLICATION

This application is a continuation of U.S. patent application Ser. No. 14/126,741, filed Dec. 16, 2013, which is a National Stage Entry of PCT/US2012/42800, filed on Jun. 15, 2012, which claims the benefit under 35 U.S.C 119(e) to U.S. Provisional Application Ser. No. 61/498,364, filed Jun. 17, 2011, the entirety of which is incorporated herein by reference.

FIELD

This relates generally to delivery devices for dermal filler threads. The delivery device is useful for delivering a thread to a patient, for example a facial wrinkle.

STATE OF THE ART

Dermal fillers have become prevalent in the field of aesthetic intervention. When dermal fillers were first studied in the 1980's, animal derived collagen fillers were most popular. However, due to skin allergies, dermal fillers of hyaluronic acid have become preferred over collagen due to fewer allergic reactions and better pliability. To date, dermal fillers approved for use in human patients to fill wrinkles consist mainly of gel compositions. Examples of these gel compositions include those made with hyaluronic acid, such as Restylane® and Juvederm®.

As gels can be difficult to deliver in a targeted manner to wrinkles in the face, more structural forms, such as a threads, are currently being investigated. As described in WO 2010/028025, to fill a wrinkle with a thread, the thread is attached to a needle at its proximal end. The distal end of the needle is then inserted through the skin surface of the subject into the dermis (or other layer) adjacent to or within the wrinkle. The needle then traverses the dermis of the subject. The needle exits the skin and by pulling the needle distally, the thread is deposited into the wrinkle. Heretofore, an effective means of attaching the thread to the needle for depositing a thread into a wrinkle has not been described.

SUMMARY

Provided is a device for delivering a dermal filler thread to a patient.

In one embodiment is provided a needle for delivering a dermal filler comprising a tubular body having a proximal portion and a distal portion, a coupler in its proximal portion for mechanically attaching a dermal filler to the needle, and a trocar in its distal portion.

In another embodiment is provided a kit comprising at least one needle for delivering a dermal filler comprising a tubular body having a proximal portion and a distal portion, a coupler in its proximal portion for mechanically attaching a dermal filler to the needle, and a trocar in its distal portion. The needle of the kit is coupled to a thread which is biocompatible and compressible. In one embodiment, the thread is comprised of hyaluronic acid, salt, hydrate or solvate thereof optionally wherein at least a portion of the hyaluronic acid, salt, hydrate or solvate thereof is cross-linked.

Further embodiments are described throughout.

DETAILED DESCRIPTION OF THE DRAWINGS

The following detailed description is best understood when read in conjunction with the drawings. It should be noted that the various features of the drawings may not be to-scale. On the contrary, dimensions of certain features are arbitrarily expanded or reduced for clarity. Included in the drawings are the following figures:

FIG. 1 is a schematic illustration of one embodiment of a needle having a coupler comprising struts.

FIG. 2 is a schematic illustration of a needle having a coupler comprising a funnel.

FIG. 19 is a schematic illustration of one embodiment of a needle having a hypotube coupler.

FIG. 20 is an exploded view of 19A from FIG. 19. The close-up shows a coupler having cleats in the shape of tabs.

FIG. 21 is a face view of a hypotube coupler.

FIG. 28A is a schematic of a needle having a detachable coupler inserted through the dermis.

FIG. 28B is a schematic of a needle having a detachable coupler inserted through the dermis with a thread attached.

Figure 30A:
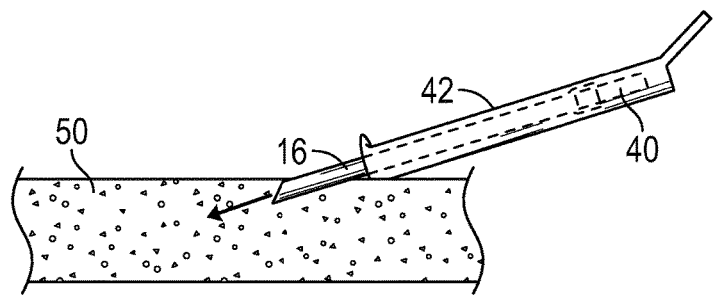
Figure 30B:
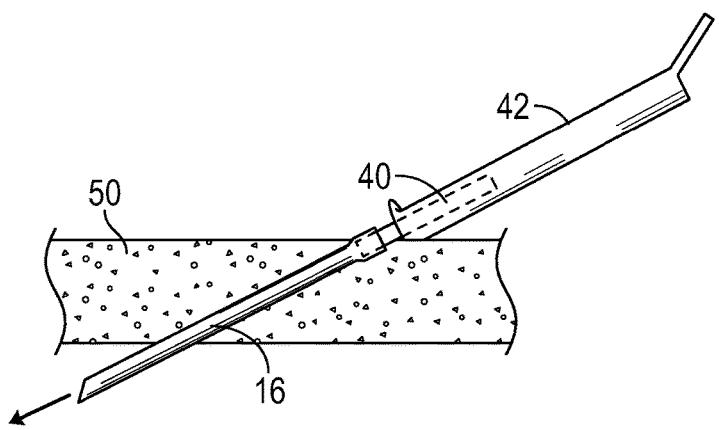
Figure 30C:
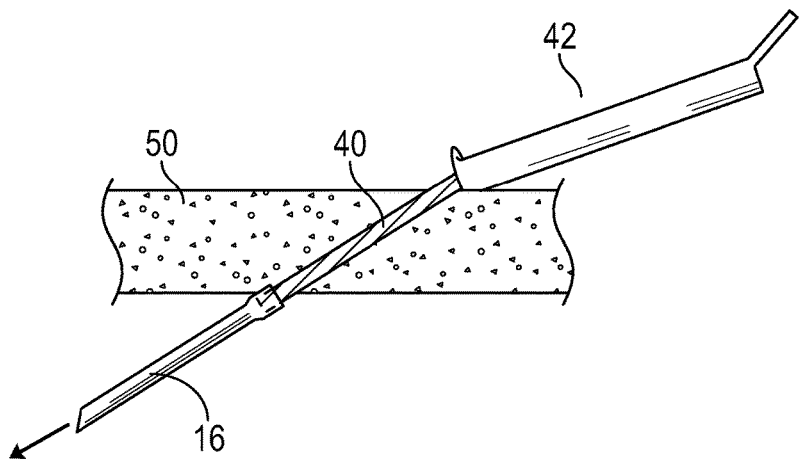

FIG. 30A, FIG. 30B, and FIG. 30C are schematics of a sheath with a pull tab and an insertion preventer as it is inserted into and pushed through the dermis.

Figure 31:
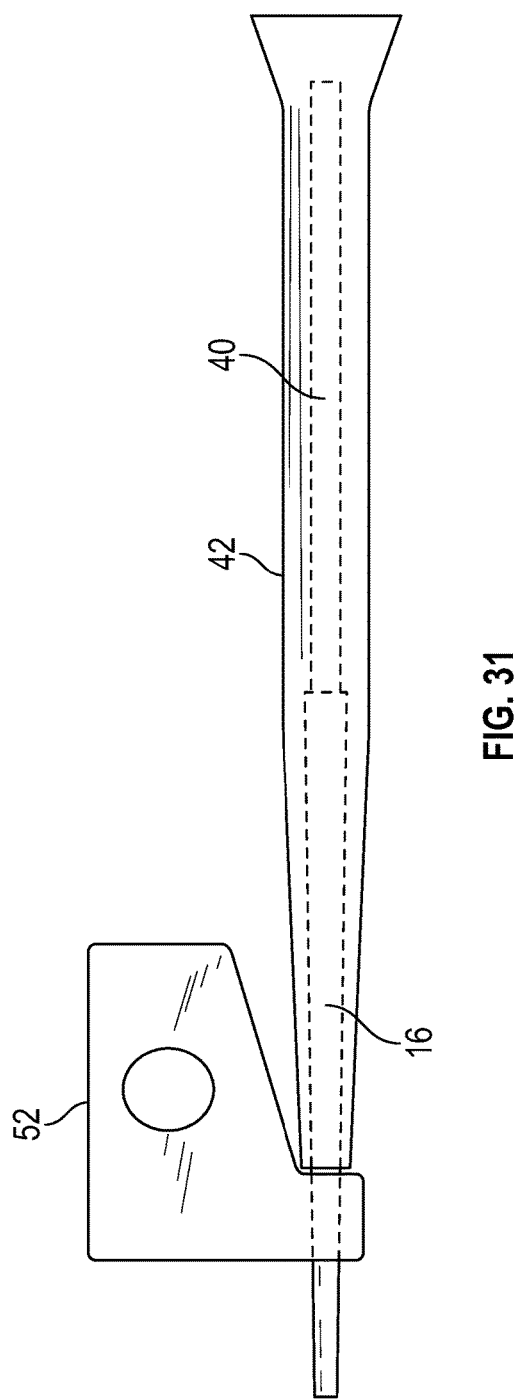

FIG. 31 is a schematic of a sheath, needle and thread further with a needle grabber.

Figure 32A:
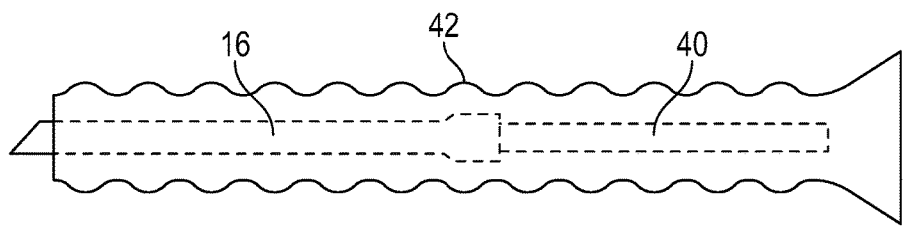
Figure 32B:
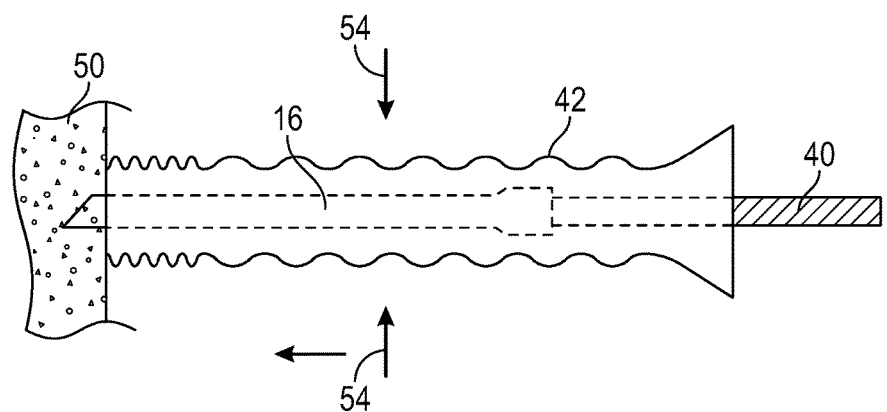

FIG. 32A and FIG. 32B are schematics of a self-buckling sheath.

Figure 33:
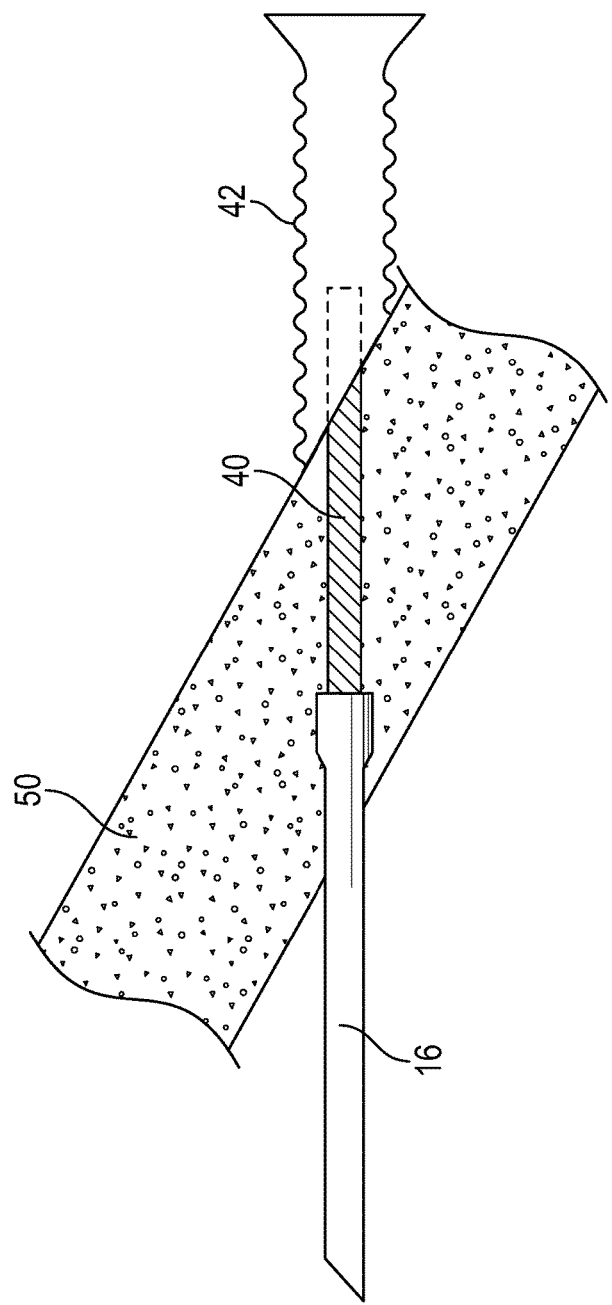

FIG. 33 is a schematic of a self-buckling sheath after insertion of the needle and thread into the dermis.

Figure 34A:
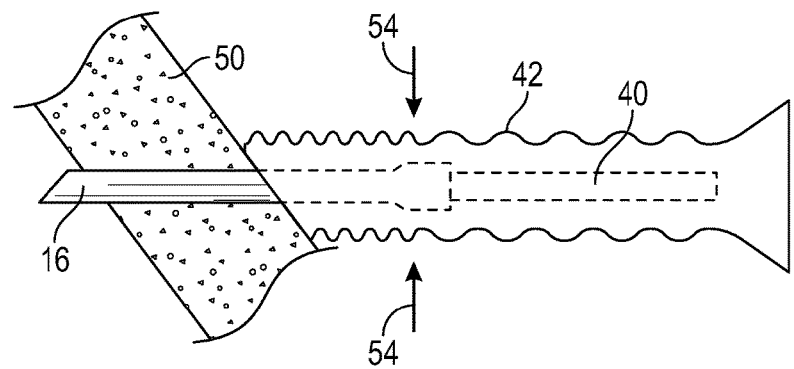
Figure 34B:
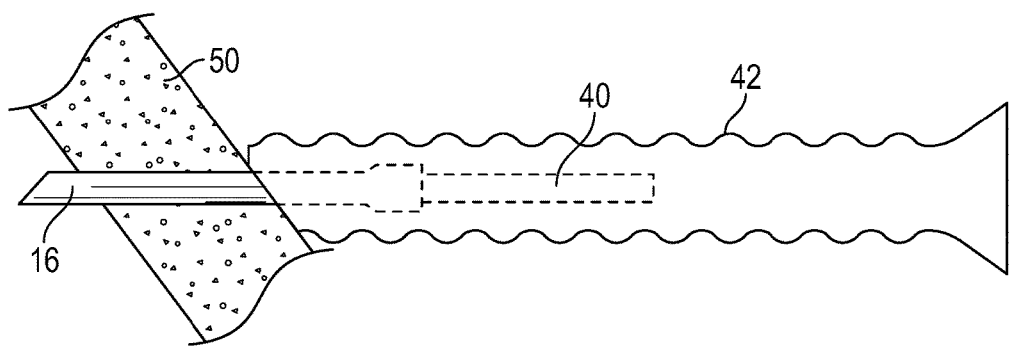

FIG. 34A and FIG. 34B are schematics of a self-buckling sheath after insertion of the needle and thread into the dermis.

Figure 35A:
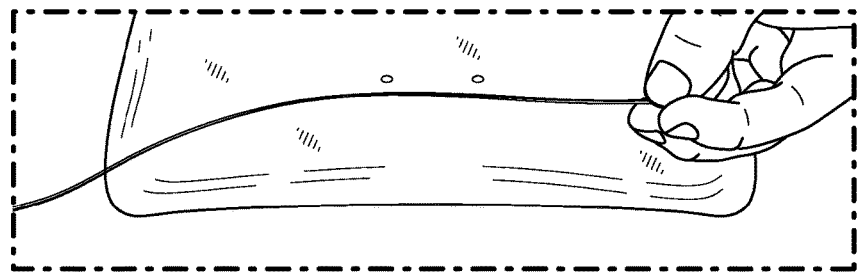

FIG. 35A shows a sheathed needle and thread.

Figure 35B:
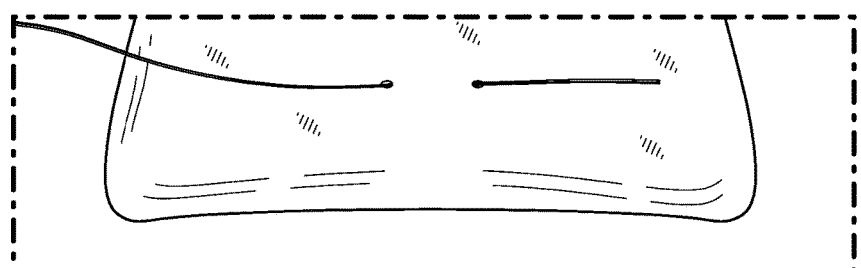

FIG. 35B shows a sheathed needle and thread inserted into puppet skin.

Figure 35C:
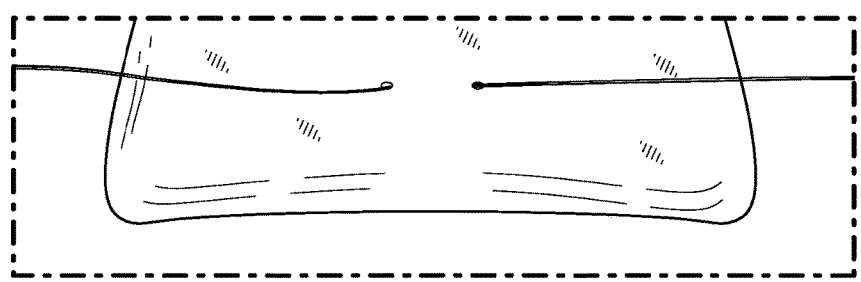

FIG. 35C shows a sheathed needle pulled through puppet skin, where the sheath is held at the insertion site, effectively removing sheath by entirely passive means.

Figure 35D:
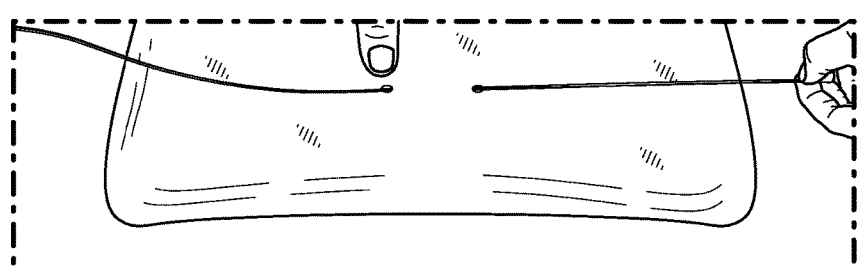

FIG. 35D shows the sheath completely removed from the needle and thread.

DETAILED DESCRIPTION

Device

Provided in FIG. 1 is one embodiment of a needle 10 having a distal portion or end 12, a proximal portion or end 14, and a tubular body 16. In some instances, the tubular body 16 may either have a lumen or be solid depending on the stiffness desired. In all instances, the tubular body will have sufficient stiffness to inserted into and through dermis, epidermis, and/or subcutaneous tissue.

The proximal portion or end 14 comprises a coupler 18 as shown in various embodiments in FIG. 1, FIG. 2, FIG. 3, FIG. 4, FIG. 5, FIG. 6, FIG. 7, FIG. 8, FIG. 9, and FIG. 11. As used herein, the terms "portion" and "end" are used interchangeably. The coupler 18 is a means for mechanically attached a thread to the needle 10 for delivery to any layer of skin. The coupler at its proximal end 20 (as shown in the figures just mentioned) has a inner diameter that is substantially the same as the outer diameter of the thread that is being attached. In one embodiment, the coupler 18 is continuous with the tubular body of the needle 10, meaning that the distal end of the needle 10 is manipulated (e.g., laser cut or crimped) to serve as the coupler 18. In another embodiment, the coupler 18 is a separate piece from the needle 10 and is affixed thereto by any number of means.

Figure 29A:
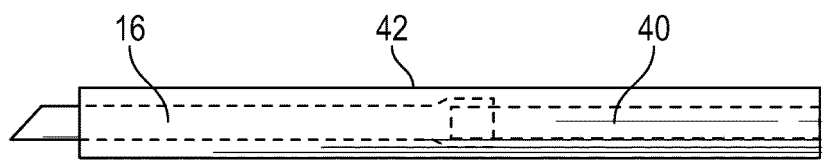
FIG. 29A is a schematic of a straight sheath.
Figure 29B:
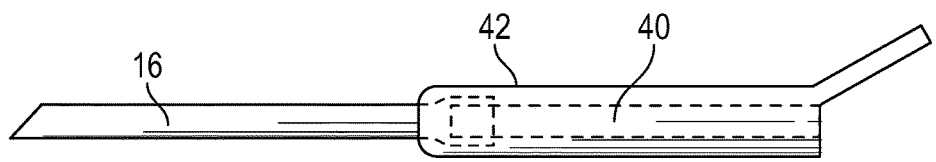
FIG. 29B is a schematic of a sheath with a pull tab.
Figure 29C:
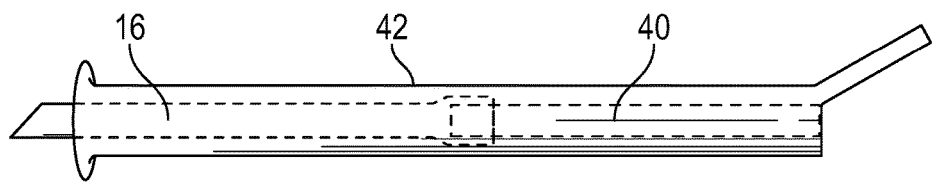
FIG. 29C is a schematic of a sheath with a pull tab and an insertion preventer.

In some embodiments, the needle 10 further comprises a sheath (FIG. 29A, FIG. 29B, and FIG. 29C). The sheath fits over the coupler 18 once the thread 10 is attached to provide additional structural support to the coupler 18. The sheath may be thin-walled heat shrink material, such as polyethylene teraphthalate (PET) or polytetrafluroethylene (PTFE).

In one embodiment, the coupler 18 is designed such that it can be expanded to a greater inner diameter and thus allow a portion of the thread to be placed into the coupler. The thread is then inserted through the length or a substantial portion of the length of the coupler. Once the thread is placed into the coupler, the expanded coupler is then crimped or closed to a diameter that fits the thread. In some instances, it is an inner diameter more similar to its unexpanded inner diameter or even smaller. The coupler 18 is crimped to an outer diameter to allow for ease of delivery through the skin but still allows the thread to maintain its structural integrity. Once this crimping occurs, the thread is mechanically attached to the coupler and thus, the needle. In one embodiment, the expansion is about 120% (i.e., from 0.010" to 0.022" inner diameter (ID)) and crimping back down to 110-150% (0.011"-0.015" ID).

Due to the design of the coupler, the thread is not easily detached from the coupler/needle during delivery to aid in the accurate positioning of the thread.

Figure 9:
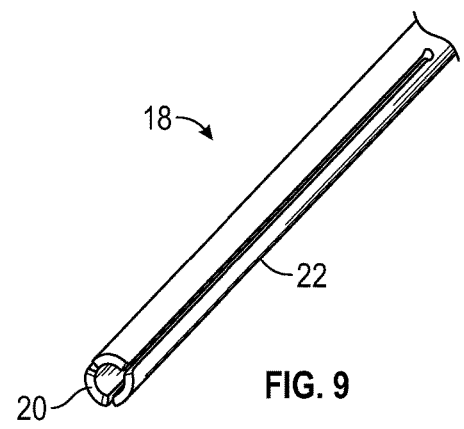
FIG. 9 is a perspective view of a coupler having slits and no struts.
Figure 10:
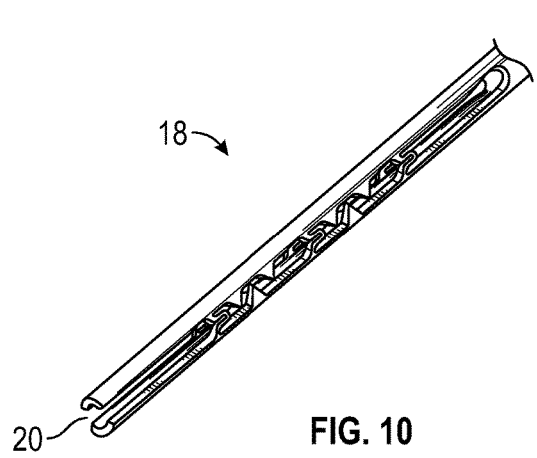
FIG. 10 is a perspective view of a coupler having struts and teeth-shaped cleats.
Figure 11:
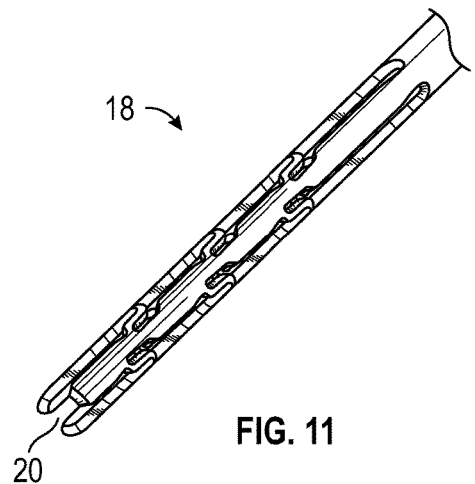
FIG. 11 is a perspective view of a coupler having three slits with staggered struts.

To aid in the ability of the coupler 18 to expand its inner diameter to place the thread, a variety of modifications may be made to the coupler. In one embodiment, one or more slits 22 are made along the longitudinal axis of the coupler. These slits 22 can be made by cutting, laser cutting, chemical etching, or stamping and rolling the coupler. In some embodiments, the coupler will have two or three slits as shown in FIG. 9. In one embodiment, each slit 22 is place about equidistant apart. Depending on whether the coupler 18 is the same or a different piece of material than the needle will determine how long the slit 22 or slits 22 may be. If the coupler is the same piece of material as the needle, the slit(s) may run the entire length of the coupler. Further, the inner edges of the slits 22 may be smooth or serrated.

Figure 3:
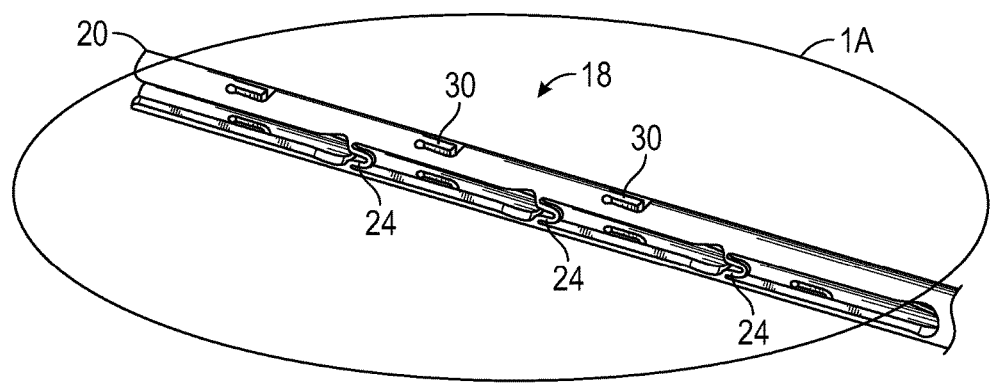
FIG. 3 is an exploded view of 1A from FIG. 1. The close-up shows a coupler having cleats in the shape of tabs.
Figure 4:
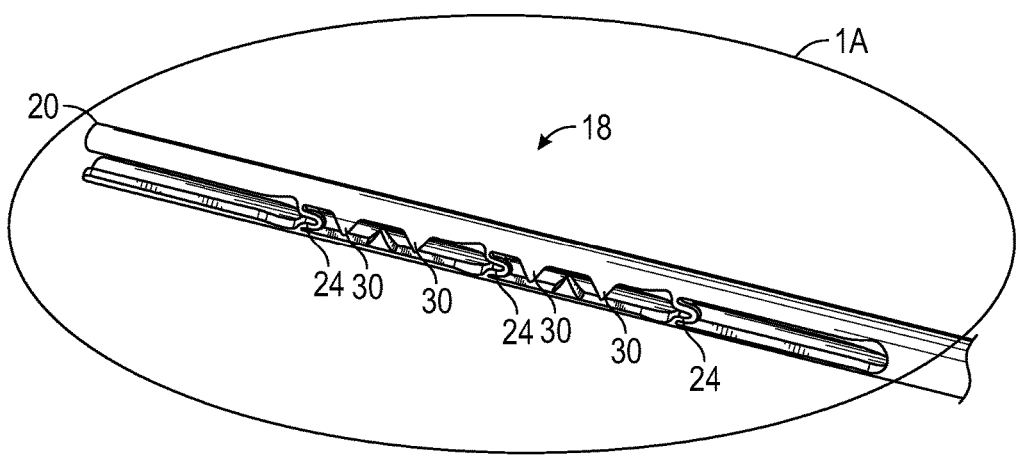
FIG. 4 is an alternative exploded view of 1A from FIG. 1. The close-up shows a coupler having cleats in the shape of teeth.
Figure 12:
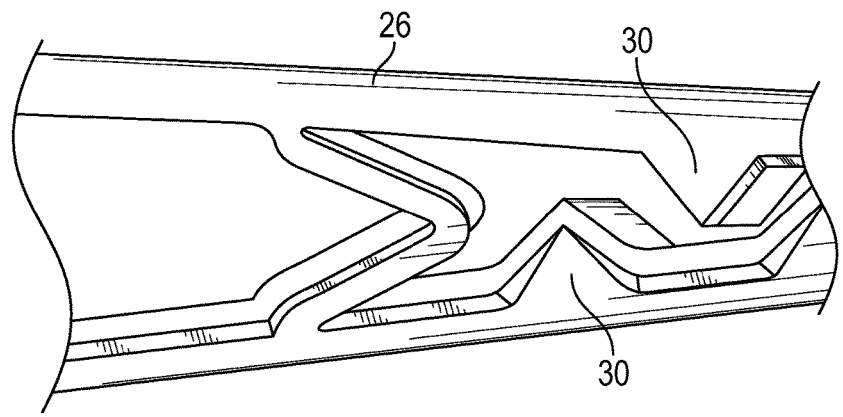
FIG. 12 is a side view of a coupler having v-shaped strut and teeth-shaped cleats.
Figure 13:
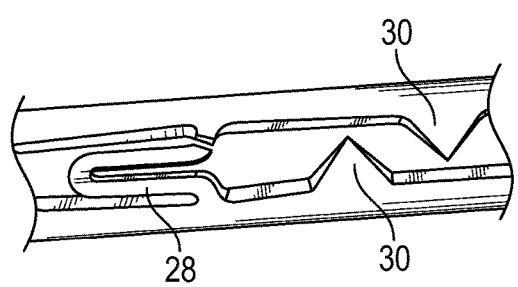
FIG. 13 is a side view of a coupler having a u-shaped strut and teeth-shaped cleats.
Figure 14:
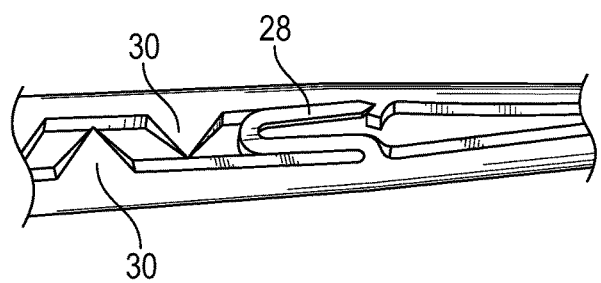
FIG. 14 is a side view of a coupler having u-shaped struts and teeth-shaped cleats.

In addition to slits, the coupler may also comprise one or more struts 24. The strut 24 is shown in FIG. 3 and FIG. 4. As shown in FIG. 12, the strut 24 can be v-shaped 26 or as shown in FIG. 13 and FIG. 14, the strut 28 can be u-shaped. Typically, the struts 24 are sized to maintain the integrity of the metal employed. In some embodiments, the ratio of the wall thickness of the coupler 18 to the width of the strut 24 at its widest part is about 1:1. The struts are similar to those used in stent design, however, in vascular stents, the struts allow a stent to be crimped down to a minimal diameter for ease of delivery through a small catheter and then expanded back to their original size. With the struts described herein, the struts allow the coupler to be expanded to receive a diameter thread that is larger than the unexpanded inner diameter. Once the thread is inserted, the struts allow the diameter to be crimped down to a small profile to be threaded through the skin.

Figure 5:
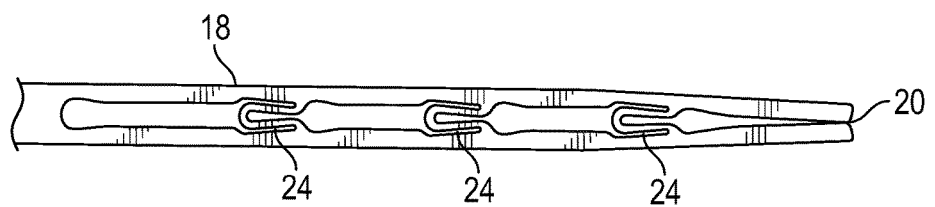
FIG. 5 is a side view of a coupler having three pairs of struts where the pairs are symmetrically placed along the longitudinal axis of the needle. This embodiment is sometimes referred to as "mirrored struts".

In some embodiments, the slits 22 in the coupler comprise one strut 24 but can comprise up to 6 or 8 struts. As shown in FIG. 5, the coupler 18 can comprise two slits 18 that are cut along the same plane. In those two slits, there are anywhere from one pair to four pair of struts. When the struts are present in even numbers, additional hoop strength is provided to the coupler. In the FIG. 5, there are 3 pairs of struts, although only three of the struts are visible in the side view. The other three struts are in the same location in the other slit, mirroring the slits in view. This is referred to as "mirrored struts." In some embodiments the mirrored struts may be offset. Thus, the needle may comprise one or more pairs of mirrored struts.

Figure 6:
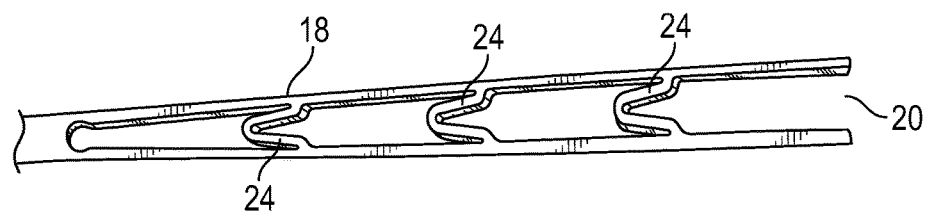
FIG. 6 is a side view of a coupler having three pairs of struts where the pairs are staggered along the longitudinal axis of the needle.
Figure 7:
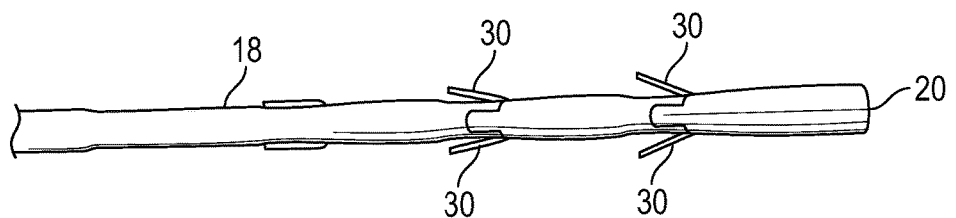
FIG. 7 is a side view of a coupler having cleats in the shape of teeth.
Figure 8:
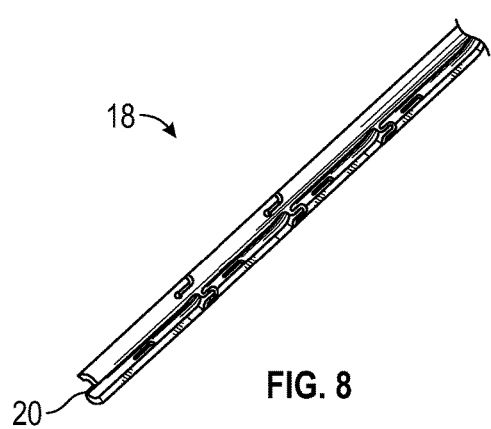
FIG. 8 is a perspective view of a coupler having tabs and struts.

FIG. 6 provides a view of one embodiment of the coupler in its expanded position. In this version of the coupler 18, there are two slits 22. In this embodiment, four struts 24 are shown. However, unlike in FIG. 5, the struts are staggered rather than mirrored. This staggered design may be employed regardless of whether there are an even or an odd number of struts.

To further aid in the coupler's ability to engage the thread, the slits 22 may also optionally comprise one or more cleats 30. The cleats 30 may be selected from a variety of shapes, including tab-shaped, like seen in FIG. 3, FIG. 8, and FIG. 11, or teeth-shaped as seen in FIG. 4, FIG. 10, FIG. 12, FIG. 13, and FIG. 14. The cleats can be separately crimped after crimping of the coupler 18 to provide improved retention of the thread by the coupler 18.

In some embodiments, the coupler comprises both struts and cleats to maximize retention of the thread. Various embodiments of a combination of struts 22 and cleats 30 may be seen in FIG. 3, FIG. 4, FIG. 8, FIG. 10, and FIG. 11.

The slits, struts and cleats may all be fashioned via laser cutting or other means.

In addition to the coupler providing the ability to be expanded, the coupler may also serve as a funnel. This is shown in FIG. 2. The thread may be extruded through the funnel and then it can dried or bonded to the inner diameter of the funnel. The funnel then is attached to the proximal end of the needle. Alternatively, the thread could be inserted and adhered with a compatible adhesive into the back end of the funnel. Any number of adhesives may be employed such as cyanoacrylate or other ultraviolet curable adhesives.

Figure 22:
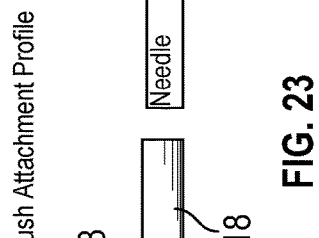
FIG. 22 is a photograph and a schematic of the side view of an angled hypotube coupler attached to a needle.
Figure 23:
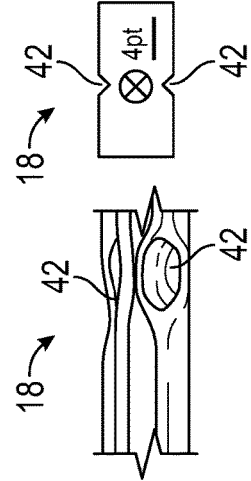
FIG. 23 is a photograph and a schematic of the side view of a flush hypotube coupler attached to a needle.

As discussed above, in some embodiments, the coupler 18 is a separate hollow, substantially tubular piece which is attached to the proximal end of the needle 10 as seen in FIG. 19, FIG. 20, FIG. 22, and FIG. 23. This substantially tubular type of coupler is herein referred to as a "hypotube coupler". As seen in FIG. 19, the proximal end of the needle is inserted at least partway, and in some embodiments about halfway, into one end of the hypotube coupler and is attached thereto by any number of means, including but not limited to, an adhesive, welding, crimping and/or heat shrink. In some embodiments, the hypotube coupler is laser welded to the proximal end of the needle. In one embodiment, the length of the hypotube coupler is about 0.2 inches (FIG. 20) and has an inner diameter of about 0.02 inches (FIG. 21). As shown in FIG. 22 and FIG. 23, the attachment profile 38 of the hypotube coupler can be angled or flush. In some embodiments, the attachment profile 38 of the hypotube coupler is angled, such that it provides gradual transition with the needle and therefore less drag through the tissue. In some embodiments, the attachment profile 38 of the hypotube coupler is flush.

Figure 24:
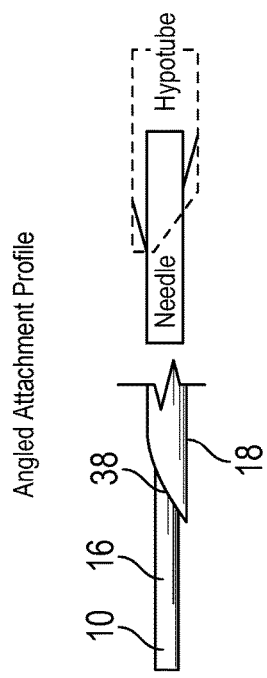
FIG. 24 is a photograph and a schematic of the side view of a hypotube coupler having eight crimp points.
Figure 25:
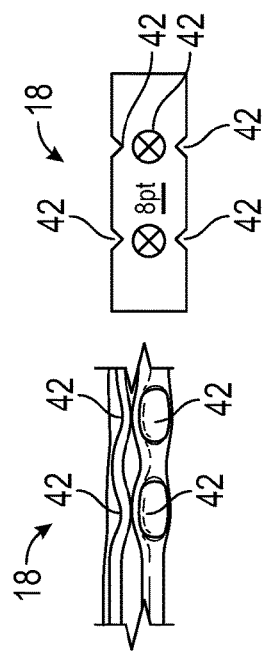
FIG. 25 is a photograph and a schematic of the side view of a hypotube coupler having four crimp points.

Once attached to the needle, at least a portion of the hypotube coupler extends beyond the proximal end of the needle for housing the thread. The thread can then be inserted into the remaining portion of the hypotube coupler and affixed thereto. Once the thread is placed into the coupler, the hypotube coupler is then crimped 42 around its circumference to immobilize the thread (see FIG. 24 and FIG. 25). In some instances, the hypotube coupler is crimped 42 at least four times around its circumference in one single plane, thus forming a "four-point crimp", to immobilize the thread (see FIG. 25). Once this crimping occurs, the thread is mechanically attached to the hypotube coupler and thus, the needle. In some embodiments, a series of at least two four-point crimps are used to secure the thread. FIG. 25 shows two four-point crimps forming an "eight-point crimp". The four-point crimp allows the use of a shorter hypotube coupler (e.g., 0.17 inches vs 0.25 inches for the eight-point crimp) with less material. The eight-point crimp demonstrates a higher pull out force (i.e., the force required to dislodge the thread from the hypotube coupler. It is contemplated that the hypotube coupler displays a pull out force of greater than about 0.400 lbf, or greater than 0.600 lbf, or greater than 0.800 lbf, or even greater than 1.00 lbf.

Figure 26:
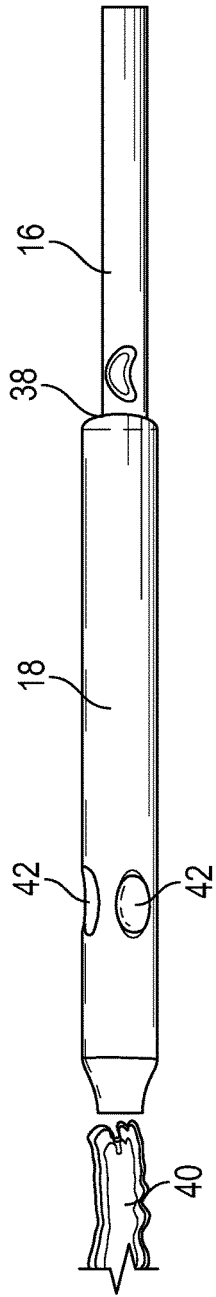
FIG. 26 is a photograph of the side view of a needle having a hypotube coupler with four crimp points attached to a thread.

In some embodiments, the cumulative drag of the needle 10 having a hypotube coupler 18 and thread 40 attached thereto (e.g., FIG. 26) is less than about 0.20 lbf-in, or less than about 0.10 lbf-in, or less than about 0.075 lbf-in, or less than about 0.060 lbf-in, or from about 0.1 to about 0.01, or from about 0.08 to about 0.04, or from about 0.075 to about 0.045 lbf-in.

Figure 27:
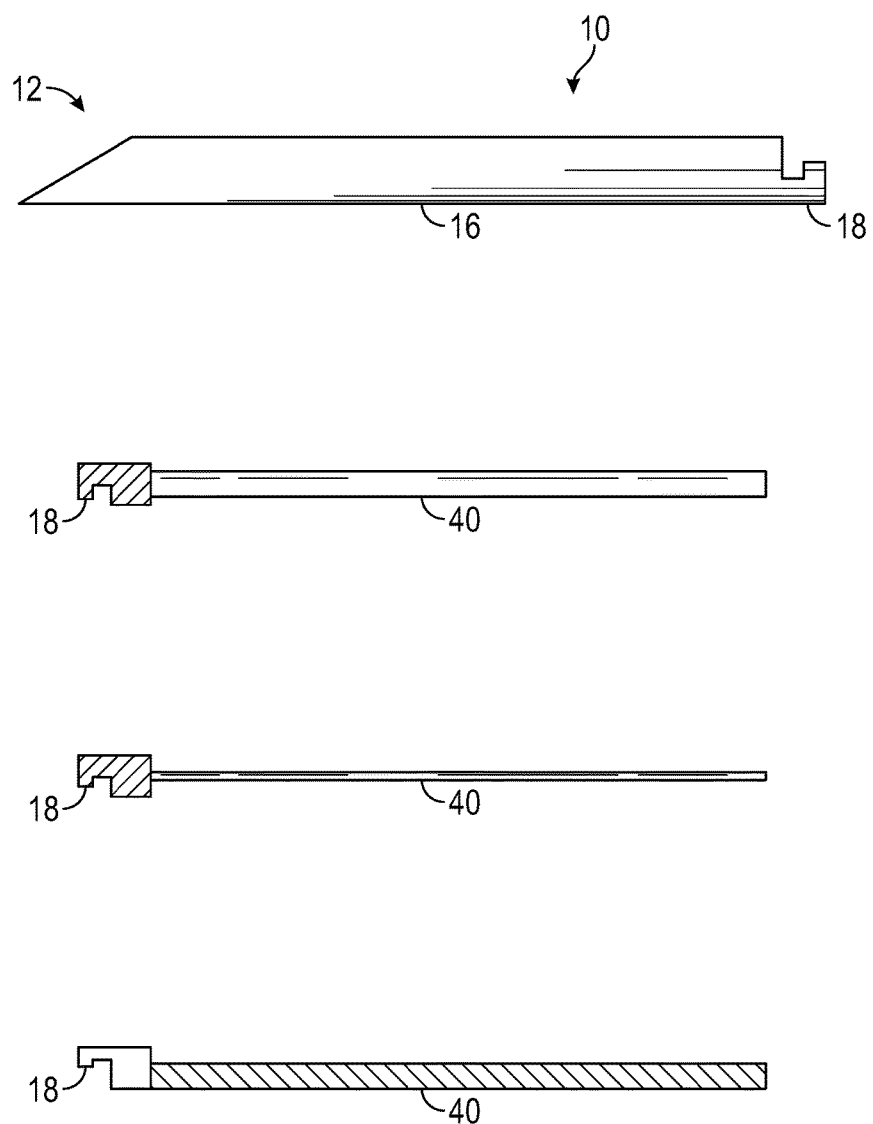
FIG. 27 is a schematic of a needle having a detachable coupler with three threads of different diameters having a coupler attached.

In certain embodiments, the design of the coupler is such that the thread is easily attached and/or detached from the coupler/needle during delivery to aid in the accurate positioning of the thread. Using such a detachable coupler allows the clinician to gauge effect by first inserting the needle 10 into the dermis 50, selecting a thread 40 having the desired thickness and then attaching the thread to the coupler 18 and pulling the thread through the dermis. See, for example, FIG. 27, FIG. 28A, and FIG. 28B.

Figure 15:
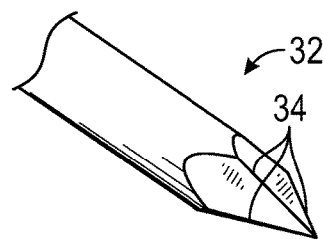
FIG. 15 is a perspective view of a trocar having three cutting edges.
Figure 16:
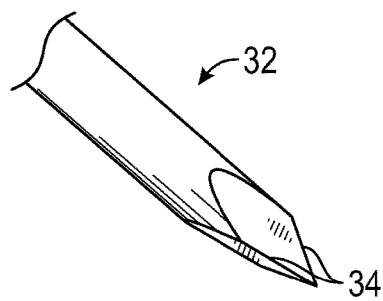
FIG. 16 is a perspective view of a trocar having four cutting edges (with only two cutting edges showing).
Figure 17:
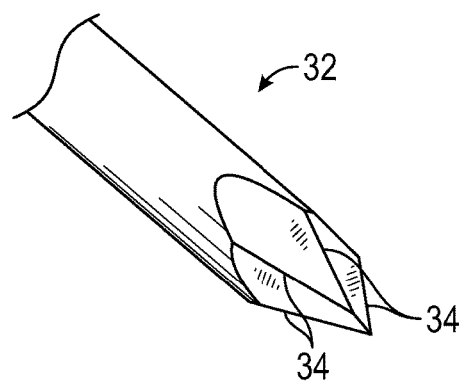
FIG. 17 is a perspective view of a trocar have four cutting edges where a pair of adjacent edges are substantially planar. The other pair is hidden.

In all embodiments of the coupler just described a variety of trocars 32 may be employed. See, for example, FIG. 15, FIG. 16, and FIG. 17. In one embodiment, the trocar has two, three (see FIG. 15), or four cutting edges. In one embodiment, the trocar has four cutting edges, which is sometimes referred to as a four-facet trocar (see FIG. 16 and FIG. 17). The four cutting edges can either be placed equidistant as seen in FIG. 16 or a pair of adjacent cutting edges can be substantially planar as seen in FIG. 17. The other adjacent pair would then also be substantially planar. When the cutting edges are substantially planar, the trocar's entry into the skin is less traumatic.

Typically, the needle 10, as well as the coupler 18 and trocar 34 are made of stainless steel. The needle may also optionally include a coating. The coating may serve to enhance the lubricity of the needle, reduce friction, and/or may serve to cover any exposed laser cut edges. The coating may be either hydrophilic or hydrophobic. In some embodiments, the coating is applied by dipping or spraying the coating onto the needle. In some embodiments, the coating is curable at room temperature and may be silicone based, such as a dispersion comprising aminofunctional polydimethylsiloxane copolymer in a mixture of aliphatic and isopropanol solvents. In another embodiment, the coating is a heat-shrinkable material, such as PET or PTFE.

While the dimensions of any component just described, it is contemplated that a 27 gauge needle that is approximately 1" to 4" in length may be employed. The inner diameter of the coupler is about 0.010" and the expanded inner diameter is about 0.021". In some embodiments, the following dimensions are also employed: 1) outer diameter of thread is from about 0.011" to about 0.020"; 2) the length of coupler is about 0.250"; 3) length of trocar is about 3.0"; 4) other suitable gauge needles include 24-30 gauge.

Threads

Figure 18:
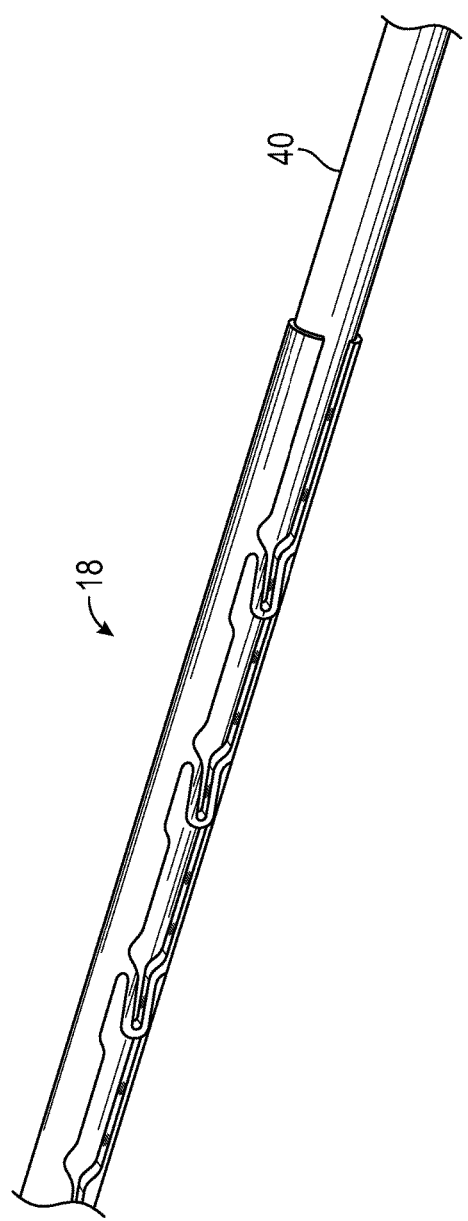
FIG. 18 is a perspective view of a thread attached or coupled to an exemplary needle described herein.

As shown in FIG. 18, a thread 40 is attached to a needle 10 at its proximal end via the coupler 18. Although it is contemplated that any thread can be used, one embodiment is directed to the needle as disclosed herein, with a biocompatible and optionally compressible thread. Biocompatible refers to the fact that a substance will not produce a toxic, injurious, or immunological response in living tissue.

For example, suitable biocompatible threads can comprise epoxies, polyesters, acrylics, nylons, silicones, polyanhydride, polyurethane, polycarbonate, poly(tetrafluoroethylene), polycaprolactone, polyethylene oxide, polyethylene glycol, poly(vinyl chloride), polylactic acid, polyglycolic acid, polypropylene oxide, poly(akylene)glycol, polyoxyethylene, sebacic acid polymers, polyvinyl alcohol, 2-hydroxyethyl methacrylate polymers, polymethyl methacrylate, 1,3-bis(carboxyphenoxy)propane polymers, lipids, phosphatidylcholine, triglycerides, polyhydroxybutyrate, polyhydroxyvalerate, poly(ethylene oxide), poly ortho esters, poly (amino acids), polycyanoacrylates, polyphophazenes, polysulfone, polyamine, poly (amido amines), fibrin, graphite, flexible fluoropolymer, isobutyl-based polymers, isopropyl styrene polymers, vinyl pyrrolidone polymers, cellulose acetate dibutyrate polymers, silicone rubber, hyaluronic acid, collagen, chondroitin sulfate, cyclodextrin, alginate, chitosan, carboxy methyl chitosan, heparin, gellan gum, agarose, cellulose, poly (glycerol-sebacate) elastomer, poly(ethylene glycol)-sebacic acid, poly(sebacic acid-co-ricinoleic acid), guar gum, xanthan gum, and combinations and/or derivatives thereof.

In certain embodiments, the threads comprise a thread of hyaluronic acid or salts, hydrates or solvates thereof or a thread of cross linked hyaluronic acid or salts, hydrates or solvates thereof or a combination thereof. Suitable hyaluronic acid threads are known in the art (see, e.g., WO/2010/028025, WO/2011/109130 and WO/2011/109129).

Accordingly, in one aspect, is provided a needle as disclosed herein attached to a thread comprised of hyaluronic acid or salts, hydrates or solvates thereof. In certain embodiments the thread is comprised of cross-linked hyaluronic acid or salts, hydrates or solvates thereof cross linked with butanediol diglycidyl ether (BDDE), divinyl sulfone (DVS) or 1-ethyl-3-(3-dimethylaminopropyl) carbodimide hydrochloride (EDC). Those of skill in the art will appreciate that many other cross-linking agents may be used to cross-link hyaluronic acid or salts, hydrates or solvates thereof. The above list of cross-linking agents is illustrative rather than comprehensive. In one embodiment, the needle as disclosed herein is attached to a thread comprised of cross-linked hyaluronic acid or salts, hydrates or solvates thereof, wherein the hyaluronic acid has been cross linked with butanediol diglycidyl ether (BDDE).

Methods of Delivering the Threads

The needles as disclosed herein, in combination with a biocompatible thread, can be used in aesthetic applications (e.g., facial contouring, dermal fillers), surgery (e.g., sutures), drug delivery, and the like.

In one aspect, provided is a method of treating a wrinkle in a subject in need thereof, A biocompatible thread is coupled to the proximal aspect of a needle as shown, for example, in FIG. 18. The distal end of the needle 10 or the trocar is then inserted through the skin surface of the subject into the dermis adjacent to or within the wrinkle and the dermis of the subject in the base of the wrinkle is traversed with the needle. Once the needle exits the skin surface of the subject, it is pulled distally until it is removed from the skin of the subject such that the thread is pulled into the location previously occupied by the needle. The excess thread is then detached from the needle at the skin surface of the subject. The detachment can be accomplished by cutting or breaking the thread at or below the surface of the skin.

In another embodiment, provided is method of providing facial contouring in a subject in need thereof. In this embodiment, the needle attached to a thread is inserted into the dermis at or adjacent to the desired treatment location, e.g., the lips, the nasolabial fold, the tear trough, etc. The needle then applies the thread to the desired area, providing facial contouring. In one embodiment, a thread is applied to various planes of the dermal tissue. In one embodiment, several threads can be placed generally parallel to each other and additional threads places in a generally perpendicular direction with respect to the first set of parallel threads thereby forming a mesh structure whose aggregate effect is to contour a larger defect or more widespread defect such as the tear trough or the infraorbital region of the eye.

Also contemplated are methods of using the needles of the invention attached to biocompatible threads, hyaluronic acid threads for example, in surgery, ophthalmology, wound closure, drug delivery, and the like.

Further Embodiments

The clinical implementation of the needles attached to biocompatible threads, such as hyaluronic acid threads, as disclosed herein differs from how injectable dermal fillers are currently delivered. For typical injectable fillers, the prefilled syringe is acquired and a sterile needle with a needle cover or cap is attached thereto. Once the needle is attached to the syringe, the needle cover or cap can be removed without the clinician coming in direct contact with the needle. With the present needle and thread, however, it may be the case that the clinician directly handles one or more of the components (i.e. the needle and/or thread) which are being inserted and/or implanted into the patient. Therefore, in some cases it may be desirable to implement a covering or sheath which can protect the entirety or a portion of the needle and thread assembly from exposure and/or contact during the insertion and implantation. FIG. 29A, FIG. 29B, and FIG. 29C show several sheath 42 constructs contemplated herein, each of which could be constructed from material amenable to e-beam sterilization, such as polyethylene terephthalate (PET), and may be colored to prevent inadvertent implantation.

FIG. 29A shows a straight sheath 42 which covers the entire needle 10 and thread 40. The straight sheath is of a diameter slightly larger than the needle and thread such that is readily removed by the clinician, but not so large that is would be displaced during routine handling. FIG. 29B shows a partial sheath 42 which houses the thread 40 without substantially housing the needle 10. In certain embodiments, the sheath can be equipped with a pull tab at the proximal end (See, e.g., FIG. 29B) which the clinician can use to pull off the sheath at the desired time. Such sheaths 42 could be removed either directly prior to or during insertion of the needle 10 and thread 40.

In certain embodiments, the sheath 42 is designed with an expanded distal edge to act as an insertion protector (FIG. 29C, FIG. 30A, FIG. 30B, and FIG. 30C) by abutting the skin as the needle is inserted into the patient while passively removing the sheath from the needle 10 and thread 40.

In certain embodiments, the sheath 42, needle 10 and thread 40 further comprise a needle grabber 52 which tightly and securely clamps the needle 10 when grasped by the fingers of the clinician, and then allows the needle to slide freely when tension is released (FIG. 31).

In certain embodiments, the sheath 42 is a self-buckling sheath such that when the needle 10 is inserted into the dermis 50, the sheath 42 buckles or cripples against the skin (FIG. 32A and FIG. 32B). As shown in FIG. 32B, as long as there is some un-buckled sheath distal to the grab point 54 (i.e., between the skin and the point at which the clinician grasps the needle), the clinician can continue to insert the needle 10 into the dermis. However, once the sheath is fully compressed distal to the grab point 54, the sheath 42 must be pulled back. In some embodiments, once buckled and the tension at the grab point is removed, the sheath 42 remains buckled (FIG. 33). In another embodiment, once buckled and the tension at the grab point is removed, the sheath 42 self-elongates (FIG. 34A and FIG. 34B).

We claim:

1. A needle for delivering a dermal filler, the needle comprising:
   a dermal filler thread;
   a tubular body having a proximal portion, a distal portion, and a longitudinal axis;
   a coupler in the proximal portion for attaching the dermal filler thread to the needle, the coupler comprising a plurality of segments extending along a longitudinal axis of the coupler, a plurality of slits aligned relative to one another and extending along the longitudinal axis of the coupler between the plurality of segments, a plurality of struts spaced apart and staggered along the longitudinal axis of the coupler, wherein each of the struts is connected to a pairing of the plurality of segments and extends across a slit of the plurality of slits; and
   a trocar in the distal portion of the tubular body;
   wherein the coupler in the proximal portion is attached to the dermal filler thread.

2. The needle of claim 1, wherein the trocar comprises two to four cutting edges.

3. The needle of claim 2, wherein the trocar comprises four cutting edges.

4. The needle of claim 3, wherein the two of the four cutting edges are substantially planar and the other two of the four are also substantially planar.

5. The needle of claim 1 wherein the dermal filler thread comprises a hyaluronic acid, salt, hydrate or solvate thereof.

6. The needle of claim 1 wherein the dermal filler thread comprises a crosslinked hyaluronic acid.

7. The needle of claim 1, wherein the plurality of struts allow the coupler to be expanded from a first diameter smaller than a diameter of the dermal filler thread to a second diameter capable of receiving the dermal filler thread.

8. A needle for delivering a dermal filler, the needle comprising:
   a tubular body having a proximal portion and a distal portion;
   at least one cutting edge in the distal portion; and
   a coupler in the proximal portion for retaining a dermal filler thread, the coupler having a longitudinal axis, a first segment and a second segment each extending along the longitudinal axis, a slit extending along the longitudinal axis between the first segment and the second segment, and a plurality of struts in which each strut extends across the slit transverse to the longitudinal axis and is connected to the first segment and the second segment.

9. The needle of claim 8, further comprising:
   a second slit extending along the longitudinal axis between the first segment and the second segment; and
   a plurality of second struts in which each second strut extends across the second slit transverse to the longitudinal axis and is connected to the first segment and the second segment.

10. The needle of claim 9, wherein the struts are spaced apart from each other along the slit, and wherein the second struts are spaced apart from each other along the second slit at the same axial locations as the struts.

11. The needle of claim 9, wherein the struts are spaced apart from each other along the slit, and wherein the second struts are spaced apart from each other along the second slit at staggered axial positions relative to the struts.

12. The needle of claim 8, wherein each of the struts is u-shaped.

13. The needle of claim 8, wherein each of the struts is v-shaped.

14. The needle of claim 8, further comprising a plurality of cleats arranged along the slit in which each cleat projects from the first segment or the second segment.

15. The needle of claim 14, wherein the plurality of cleats comprises a first plurality of cleats projecting from the first segment and a second plurality of cleats projecting from the second segment, wherein the first plurality of cleats are interleaved with the second plurality of cleats.

16. The needle of claim 8, wherein the plurality of struts allows the coupler to be expanded from a first diameter to a second diameter larger than the first diameter.

17. The needle of claim 16, wherein the coupler is substantially tubular and has an inner diameter for receiving the dermal filler thread that is configured to expand from the first diameter to the second diameter.

18. A needle for delivering a dermal filler, the needle comprising:
   a tubular body having a proximal portion and a distal portion;
   a trocar in the distal portion; and
   a coupler in the proximal portion comprising an inner diameter, a longitudinal axis, a plurality of slits extending along the longitudinal axis, and a plurality of struts each extending transverse to the longitudinal axis, wherein the plurality of slits and the plurality of struts permit the coupler to expand the inner diameter to receive a dermal filler thread.

19. The needle of claim 18, wherein the plurality of slits and the plurality of struts are configured to permit the coupler to expand from an unexpanded position in which the inner diameter is less than a diameter of the dermal filler thread to an expanded position in which the inner diameter is larger than the dermal filler thread.

20. The needle of claim 18, wherein the plurality of struts permit the plurality of slits to be expanded with expansion of the inner diameter.

\* \* \* \* \*